US012582785B2

(12) United States Patent
Ono

(10) Patent No.: US 12,582,785 B2
(45) Date of Patent: Mar. 24, 2026

(54) DRUG INHALER AND COUNTER MECHANISM

(71) Applicant: NIPPHARMA CO., LTD., Tokyo (JP)

(72) Inventor: Shinichi Ono, Tokyo (JP)

(73) Assignee: NiPPharma Co., Ltd., Tokyo (JP)

( * ) Notice: Subject to any disclaimer, the term of this patent is extended or adjusted under 35 U.S.C. 154(b) by 567 days.

(21) Appl. No.: 18/253,216

(22) PCT Filed: Oct. 12, 2021

(86) PCT No.: PCT/JP2021/037783
§ 371 (c)(1),
(2) Date: May 17, 2023

(87) PCT Pub. No.: WO2022/107502
PCT Pub. Date: May 27, 2022

(65) Prior Publication Data
US 2024/0299679 A1 Sep. 12, 2024

(30) Foreign Application Priority Data
Nov. 19, 2020 (JP) ................................. 2020-192801

(51) Int. Cl.
A61M 15/00 (2006.01)

(52) U.S. Cl.
CPC ... A61M 15/0073 (2014.02); *A61M 2202/064* (2013.01)

(58) Field of Classification Search
CPC ............ A61M 2202/064; A61M 15/00; A61M 15/0051; A61M 15/0068; A61M 15/0071; A61M 15/0073
See application file for complete search history.

(56) References Cited

U.S. PATENT DOCUMENTS 7,089,935 B1 * 8/2006 Rand ................. A61M 15/0043
128/203.15
7,793,798 B2 * 9/2010 Stradella ............... G06M 1/045
128/200.23
(Continued)

FOREIGN PATENT DOCUMENTS

GB 1336014 A 11/1973
JP 2004-512147 A 4/2004
(Continued)

OTHER PUBLICATIONS

International Search Report of International Patent Application No. PCT/JP2021/037783 completed on Oct. 27, 2021 and mailed Nov. 9, 2021 (4 pages).
(Continued)

*Primary Examiner* — Brandy S Lee
*Assistant Examiner* — Mishal Zahra Hussain
(74) *Attorney, Agent, or Firm* — Pyprus Pte Ltd; George Liu

(57) ABSTRACT

[Problem] To provide a drug inhaler equipped with a counter mechanism having a simple and compact configuration. [Solution] In this inhaler 100, a mount is gradually peeled off one or a plurality of blister strips in coordination with the operation of a blister opening means, and an amount of a powdered drug corresponding to a single dose is sequentially fed to a space enabling inhalation through an inhalation port 41. The inhaler 100 has a counter mechanism for presenting the remaining number of the drug that is individually packaged by the blister strip in coordination with the operation of the blister opening means. The counter mechanism includes: a counter dial 50 in which a spiral-shaped rack gear 52a is formed on the reverse surface side, and information indicating the remaining number of the drug is displayed so as to be arranged in a spiral shape along the rack gear 52a on the obverse surface side; and a pinion gear 60 that fits with the rack gear 52a and that rotates in a given direction in coordination with the operation of the blister opening means.

4 Claims, 5 Drawing Sheets

(56)  References Cited

U.S. PATENT DOCUMENTS

|  |  |  |  |  |
|---|---|---|---|---|
| 8,375,941 | B2 * | 2/2013 | King | A61M 15/0051 |
|  |  |  |  | 221/92 |
| 9,987,440 | B2 * | 6/2018 | Åberg | A61M 15/0016 |
| 2005/0126469 | A1 * | 6/2005 | Lu | G06M 1/163 |
|  |  |  |  | 116/307 |
| 2015/0297841 | A1 * | 10/2015 | Ono | A61M 15/0055 |
|  |  |  |  | 128/203.15 |
| 2016/0175547 | A1 * | 6/2016 | Nakamura | A61M 15/0016 |
|  |  |  |  | 128/203.15 |

FOREIGN PATENT DOCUMENTS

| JP | 2006-519141 A | 8/2006 |
|---|---|---|
| JP | 2007-513670 A | 5/2007 |
| JP | 2007-526562 A | 9/2007 |
| JP | 2009-502287 A | 1/2009 |
| JP | 2014-113260 A | 6/2014 |

OTHER PUBLICATIONS

Written Opinion of International Patent Application No. PCT/JP2021/037783 completed on Oct. 27, 2021 and mailed Nov. 9, 2021 (3 pages).

* cited by examiner

DRUG INHALER AND COUNTER MECHANISM

TECHNICAL FIELD

The present invention relates to an inhaler for inhaling powdered drug individually packed in a blister strip. To describe specifically, the present invention includes a counter mechanism for presenting the number of remaining uses of a drug to a user.

BACKGROUND ART

Conventionally, for example, there has been known an inhaler for causing a patient to inhale a drug to suppress an inflammation of, for example, a respiratory tract, and accelerate extension of a bronchus (for example, Patent Documents 1 to 4). Since the drug inhaler is to directly administrate powdered drug to a respiratory tract and a lung as an inflamed affected part using inspiratory force of a patient himself/herself, there are advantageous in that even a small amount of drug can be concentratedly applied over the affected part, generation of a side effect can be inhibited, and expression of an effect quickens.

A general inhale device is accommodated with one or a plurality of blister strips wound in a whirl shape. As illustrated in FIG. 5, a strip-shaped blister strip 200 in which drugs are sealed is configured by bonding mutual inner surfaces of a long base portion sheet 210 and a backing sheet 220. Additionally, the base portion sheet 210 includes a plurality of blisters 211 forming spaces to seal the drugs at constant intervals in its longitudinal direction. Each of the blisters 211 contains the desired drug by an amount appropriate for one administration. At the administration, the backing sheet 220 is gradually torn off from the base portion sheet 210 such that the appropriate amount of drugs are exposed. Note that the blister strip 200 in the inhaler seals a drug for a respiratory disease treatment, such as asthma, chronic obstructive pulmonary disease (COPD), bronchitis, or chest infection. Note that it is only necessary to use the publicly known drug. Especially, Patent Document 2 discloses an inhaler that allows taking out drugs from two respective blister strips and mixing the drugs in a manifold.

Additionally, Patent Document 2 to Patent Document 4 disclose a counter mechanism for presenting the number of remaining drugs. The counter mechanism is in conjunction with a cover for opening and closing a suction port and a peeling mechanism for tearing off a backing sheet from a blister strip. Specifically, when the suction port cover is opened, the backing sheet is partially torn off from the blister strip by the peeling mechanism, and a drug by one dose amount is taken out from the blister strip. Then, simultaneously with this, the number of remains presented by the counter mechanism decreases by one.

Patent Document 1: JP-T-2004-512147
Patent Document 2: JP-T-2009-502287
Patent Document 3: JP-T-2007-526562
Patent Document 4: JP-A-2014-113260

DISCLOSURE OF THE INVENTION

Problems to be Solved by the Invention

For example, the counter mechanism disclosed in Patent Document 3 indicates ones place and tens place by different dials. That is, when the dial indicating the ones place rotates by one, the dial indicating the tens place is turned by a predetermined angle to carry the number indicated by the tens place by one. However, when the number of remains of two digits is presented by the two dials, there are problems that the structure of the counter mechanism is complicated and this inhibits downsizing of the inhaler. Additionally, a problem that when a failure occurs in any one of the ones place dial and the tens place dial, the number of remains cannot be accurately presented is conceivable. Especially, while the inhaler handles a fine powdered drug, when the number of dials or gears constituting the counter mechanism increases, microparticles of the drug are interposed between the respective dials and gears, and it is concerned that a failure that the counter mechanism fails to appropriately function occurs.

In contrast to this, for example, as shown in Patent Document 4, to simplify the structure of the counter mechanism, the number of remains of two or more digits can be represented in the proximity of an outer periphery of one dial. However, in the case, as the number of remains that should be represented increases, the diameter of the dial becomes large. As a result, a problem that the entire size of the inhaler increases and this greatly limits the design layout of the inhaler arises.

Therefore, a main object of the present invention is to provide a counter mechanism having a simple and compact configuration.

Solutions to the Problems

As a result of serious examination of the solution for the problems accompanied by the conventional invention by the inventor of the present invention, knowledge that representation of information displaying the number of remaining drugs or the like in a spiral pattern on a disc-shaped dial allows presenting the large number of remains even with one dial having a small diameter has been obtained. Then, it has been conceived that, by disposing a mechanism to turn the dial according to, for example, an operation of blister opening means including a suction port cover, a lever, or the like, the simple and compact counter mechanism can be achieved, thus completing the present invention. To describe specifically, the present invention has the following configurations.

A first aspect of the present invention relates to an inhaler of powdered drug. The inhaler according to the present invention includes blister opening means that tears off a backing sheet from a blister strip to open a blister. The blister opening means, for example, may tear off the backing sheet from the blister strip in conjunction with an open/close operation of a suction port cover that opens and closes a suction port, or may tear off the backing sheet from the blister strip in conjunction with a raise and lower operation of a lever disposed separately from the suction port cover. Thus, the inhaler gradually tears off the backing sheet from one or a plurality of the blister strips by the blister opening means and sequentially supplies powdered drug by one dose amount to a space configured to inhale through the suction port. That is, the inhaler of the present invention may take out the drug by one dose amount from one blister strip, or may take out the drugs from the two or more respective blister strips and mix them to prepare one dose amount. Additionally, the inhaler according to the present invention includes a counter mechanism for presenting the number of remaining drugs individually packed by the blister strip in conjunction with the operation of the blister opening means. Note that "the number of remains" may be indicated by a countdown method that gradually decreases the number of remains to 0, or may be indicated by a count up method that gradually increases the number of remains from 0. Even with the count up method, the number of drugs is obviously limited and the maximum number is determined. Therefore, when the maximum number is preliminarily notified to a user, the number of remaining drugs can be presented to the user. Note that when the number of remaining blisters becomes 0, a counter dial may be disabled to rotate any further to stop a drive system.

The counter mechanism of the inhaler includes the counter dial and a pinion gear. The counter dial has a disk shape, and has a back surface side on which the rack gear in a spiral pattern is formed and a front surface side on which information displaying the number of remaining drugs are aligned in a spiral pattern and represented along the rack gear. Note that as the "information displaying the number of remaining drugs," information presenting means, such as number, a character, a drawing, a color, or a sign, only needs to be represented on the front surface of the counter dial by the publicly known representation method, such as printing or marking. The pinion gear is fitted to the rack gear and turns in a constant direction in conjunction with the operation of the blister opening means. Although a rotation shaft of the pinion gear is fixed and a position of the pinion gear is immovable, turning the pinion gear moves the counter dial. Thus, among a plurality of pieces of the information displaying the number of remains represented on the counter dial, the information that has reached a specific position (for example, immediately above the rotation shaft of the pinion gear) being the actual number of remains can be presented. Thus, in the present invention, the large number of numbers or the like is aligned in the spiral pattern and represented on the counter dial. Therefore, for example, even when the number of remains of two or more digits is presented, the number or the like can be consolidated to one counter dial having a small diameter to be represented. Since this eliminates the need for disposing two counter dials or disposing a dial having a large diameter to present the number of remains of two or more digits as in the prior art, simplification and downsizing of the structure of the counter mechanism can be achieved.

In the inhaler according to the present invention, a housing of the inhaler preferably includes a window portion for visually perceiving one piece of the information displaying the number of remaining drugs represented on the counter dial from outside the housing. This allows presenting the number of remaining drugs in an aspect of easily understood by the user.

In the inhaler according to the present invention, the counter mechanism preferably further includes a slide lane that restricts a movement direction of the counter dial to a constant direction when the pinion gear turns. Thus, by disposing the slide lane to restrict the movement direction of the counter dial, the number of remains can be stably presented and a blank space prepared in advance for movement of the counter dial can be minimized.

A second aspect of the present invention relates to the counter mechanism. The counter mechanism according to the second aspect of the present invention can be widely used as means to present any number of uses, in addition to the counter mechanism for the inhaler. To describe specifically, the counter mechanism includes a counter dial and a pinion gear. The counter dial has a back surface side on which a rack gear in a spiral pattern is formed and a front surface side on which information displaying the number of usages is aligned in a spiral pattern and represented along the rack gear. The pinion gear is fitted to the rack gear and turns in a constant direction in conjunction with a use operation.

Advantageous Effects of the Invention

With the present invention, the counter mechanism having the simple and compact configuration can be provided.

DESCRIPTION OF PREFERRED EMBODIMENTS

The following describes configurations to carry out the present invention using the drawings. The present invention is not limited to the configurations described below, but includes those appropriately changed from the configurations below by a person skilled in the art within an obvious range.

Figure 1:
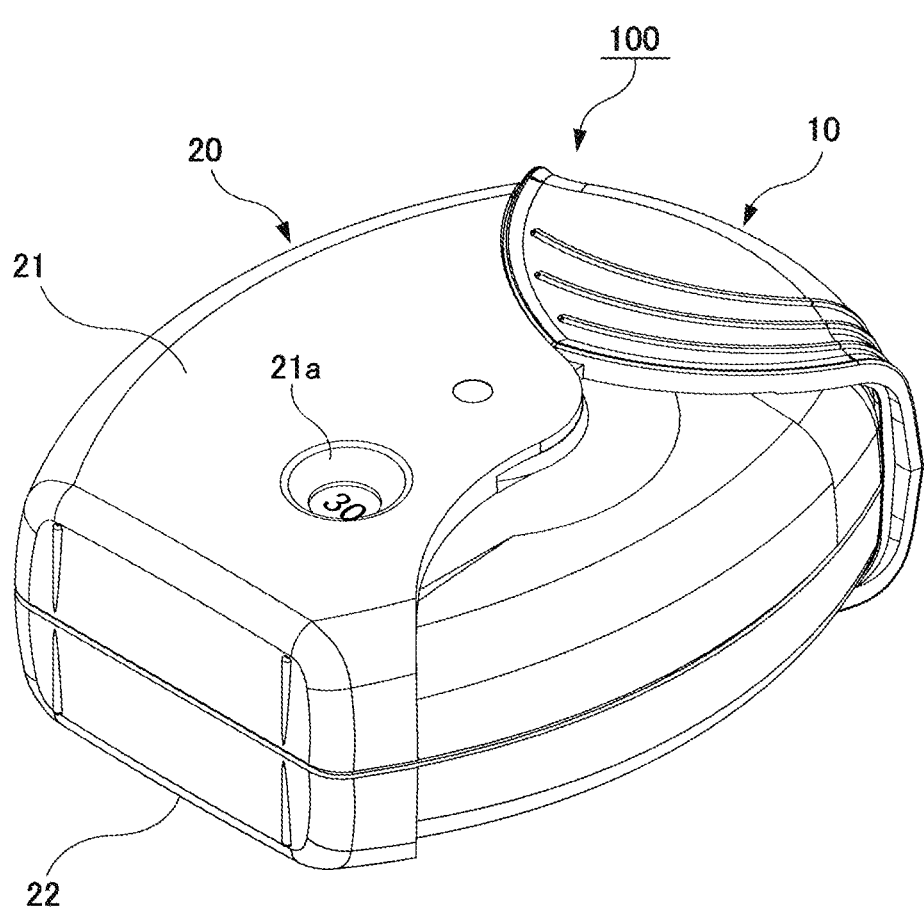
FIG. 1 is a perspective view illustrating an inhaler of one embodiment according to the present invention from a front surface side.
Figure 5:
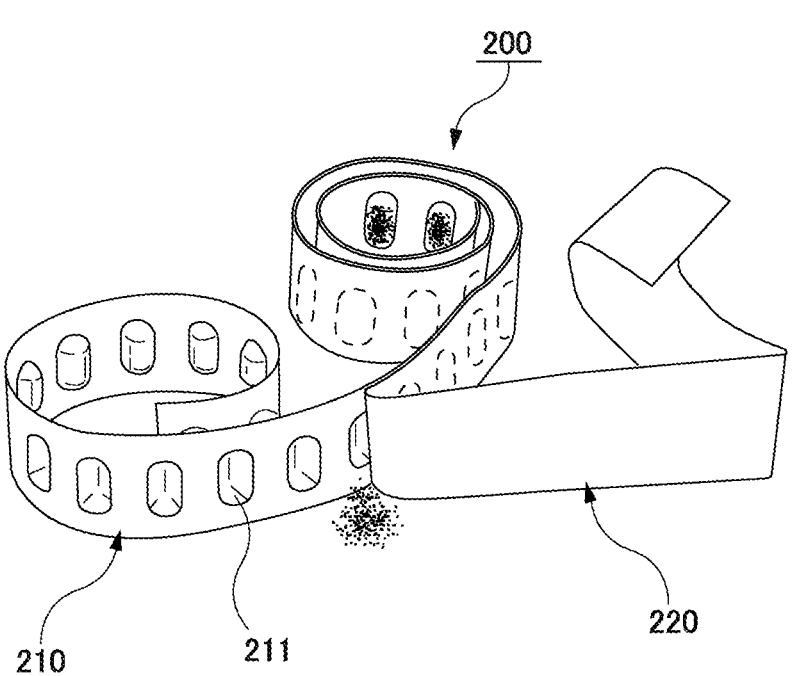
FIG. 5 illustrates an outline of a blister strip accommodated in the inhaler.

FIG. 1 illustrates an inhaler 100 of one embodiment according to the present invention. Two blister strips 200 (see FIG. 5) are accommodated inside a housing 20 of the inhaler 100 illustrated in FIG. 1. In the inhaler 100, opening a suction port cover 10 mounted on the housing 20 exposes a suction port of a drug. Additionally, an open/close operation of the suction port cover 10 is in conjunction with a peeling mechanism inside the housing 20. Thus, in this embodiment, the blister opening means is configured by the suction port cover 10 and the peeling mechanism. Opening the suction port cover 10 partially tears off the backing sheet 220 of the two blister strips 200 by the peeling mechanism, and the powdered drug taken out from a blister 211 of the base portion sheet 210 is supplied to a manifold and is mixed inside of the manifold. The mixed drug can be inhaled through the suction port. The peeling mechanism in conjunction with the suction port cover 10 is already publicly known as described in, for example, Patent Document 1 to Patent Document 4, and various kinds of peeling mechanisms publicly-known at the time of application can be appropriately employed also in the inhaler 100 according to the present invention. In view of this, Description of this application omits the illustration and description of details of the peeling mechanism of the blister strip 200.

Additionally, as illustrated in FIG. 1, the housing 20 is configured by combining a top cover 21 and a bottom cover 22 and forms an accommodation space of the blister strip 200 and another internal mechanism. The top cover 21 is a cover member covering the front surface side of the inhaler 100, and a window portion 21a penetrating the cover in a thickness direction is formed in a part of the top cover 21. A user can visually check the number of remaining drugs presented by the counter mechanism accommodated in the housing 20 through the window portion 21*a* of the top cover 21 (in the example illustrated in FIG. 1, it is presented that the number of remaining drugs is "30"). The counter mechanism is in conjunction with the above-described suction port cover 10 or peeling mechanism. When the suction port cover 10 in the close state is opened, the number of remains presented by the counter mechanism is counted down (or counted up) by one. The present invention features in the counter mechanism presenting the number of remaining drugs or the like. Therefore, the following will describe the specific content of the present invention, mainly the counter mechanism, in detail.

Figure 2:
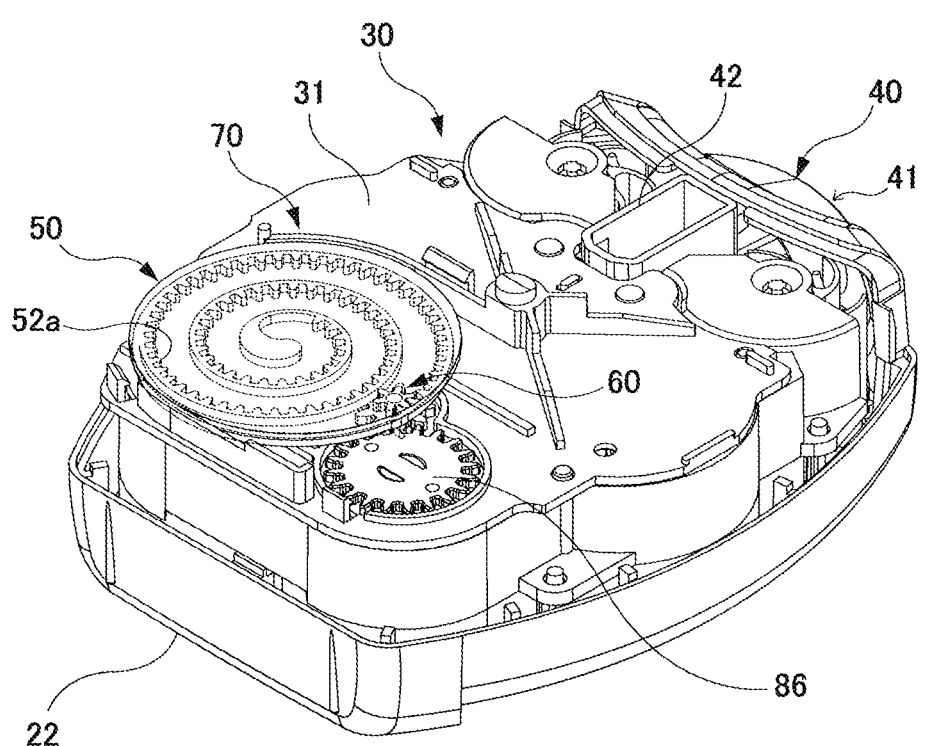
FIG. 2 illustrates a state in which a suction port cover and a top cover are removed from the inhaler illustrated in FIG. 1.

FIG. 2 illustrates a state in which the suction port cover 10 and the top cover 21 are removed from the inhaler 100 illustrated in FIG. 1. As illustrated in FIG. 2, the housing 20 internally includes a casing 30 mainly accommodating the two blister strips 200 and the peeling mechanism thereof, and a mouthpiece 40 including a suction port 41 communicating with a manifold 42 is disposed on the inhale side of the casing 30. Note that an upper lid 31 positioned on the top cover 21 side and a bottom lid 32 positioned on the bottom cover 22 side are combined to configure the casing 30. In the inhaler 100 of the present invention, opening the suction port cover 10 exposes the mouthpiece 40 in which the suction port 41 is formed. The user breathes in while taking the mouthpiece 40 into his/her mouth to ensure inhaling the two kinds of drugs mixed in the manifold 42 through the suction port 41. Note that the mouthpiece 40 and the manifold 42 can be different components or can be an integrated component.

Figure 3:
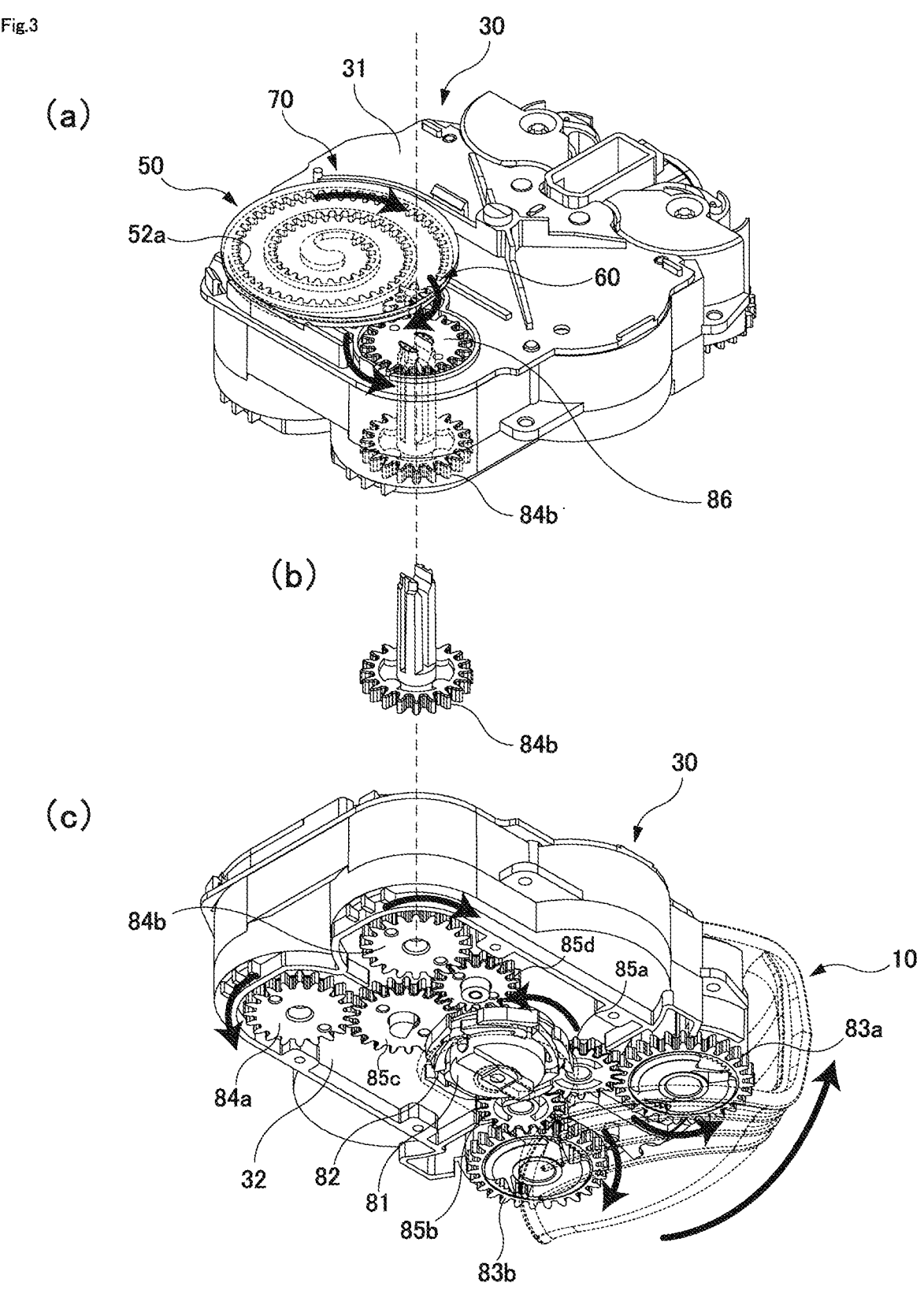
FIG. 3 illustrates an example of an internal structure around a counter mechanism of the inhaler of one embodiment according to the present invention.
Figure 4:
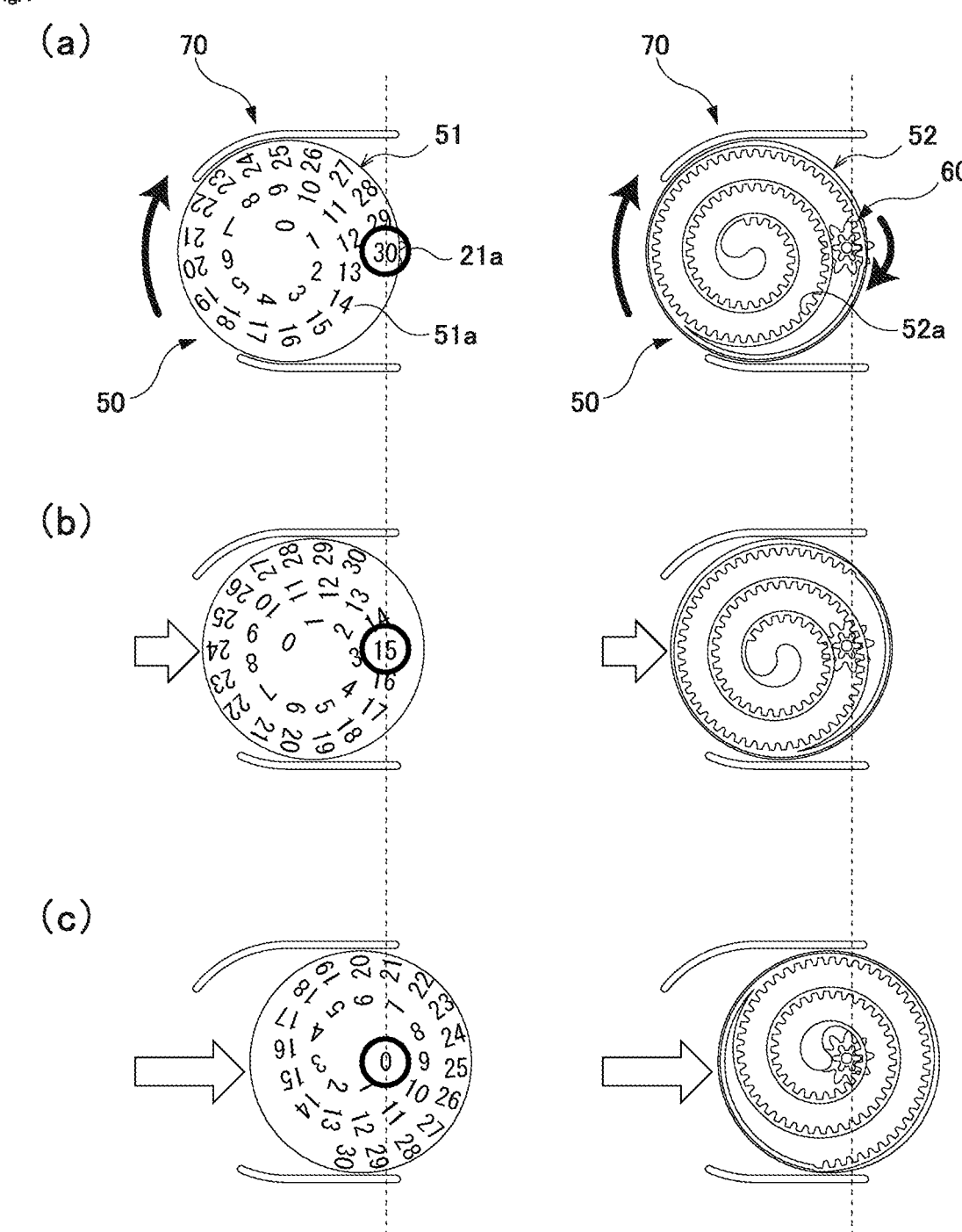
FIG. 4 schematically illustrates a structure of the counter mechanism of one embodiment according to the present invention.

Next, as illustrated in FIG. 2 to FIG. 4, the inhaler 100 includes the counter mechanism for presenting the number of remaining drugs to the user. Similarly to the peeling mechanism, the counter mechanism is in conjunction with opening and closing the suction port cover 10. By causing the suction port cover 10 to transition from the closed state to the open state, the number of remaining drugs is counted down (or counted up). FIG. 3(*a*) is a perspective view on the front surface side illustrating a state of removing the suction port cover 10 and the housing 20 from the inhaler 100, and FIG. 3(*a*) is a perspective view of the back side in the same state. FIG. 3(*a*) mainly illustrates the counter mechanism, and FIG. 3(*b*) illustrates a conjunction mechanism for causing the counter mechanism to coordinate with the operation of the suction port cover 10. Additionally, FIG. 4 extracts and schematically illustrates respective elements for clear illustration of operations of the respective elements constituting the counter mechanism. FIG. 4(*a*) mainly illustrates the front surface side of the counter mechanism, and FIG. 4(*b*) mainly transparently illustrates the back side of the counter mechanism.

As illustrated in each drawing, the counter mechanism includes a counter dial 50 and a pinion gear 60 as main components. Additionally, the counter mechanism includes a slide lane 70 as a preferred element. In this embodiment, the elements 50, 60, 70 constituting the counter mechanism are disposed on the upper lid 31 side of the casing 30, specifically, between the upper lid 31 of the casing 30 and the top cover 21 of the housing 20.

The counter dial 50 is a disk-shaped member, has a front surface 51 on which information presenting means, such as numbers, characters, drawings, colors, or signs indicating the number of remaining drugs 51*a*, are aligned in a spiral pattern and represented, and a back surface 52 on which a rack gear 52*a* in a spiral pattern is formed corresponding to the alignment of the information presenting means. In the example illustrated in FIG. 4, the maximum number of usages of the drug is "30," the number "0" (zero) is represented in the proximity of the center of the front surface 51 of the counter dial 50, and the numbers from "0" to "30" are aligned and represented from there so as to extend in a spiral pattern in the outer peripheral direction. In this case, the counter mechanism first presents "30" as the maximum number of usages of the drug to the user, and each time opening and closing of the suction port cover 10 are repeated, the number of remaining drugs presented by the counter mechanism is counted down to "0." On the contrary, the number "30" corresponding to the maximum number of usages can be represented in the proximity of the center of the counter dial 50, and the numbers from "30" to "0" can be aligned and represented from there so as to extend in a spiral pattern in the outer peripheral direction. In this case, the number of remains is counted up from "0" to "30." Additionally, the rack gear 52*a* in the spiral pattern is formed corresponding to the above-described row of the numbers on the back surface 52 of the counter dial 50. Specifically, when it is assumed that the numbers are connected with an imaginary line in the ascending order or the descending order, the rack gear 52*a* in the spiral pattern same as the spiral formed by the imaginary line is formed immediately below the imaginary line.

The pinion gear 60 is a circular gear having a small bore fitted to the rack gear 52*a* formed on the back surface 52 of the counter dial 50. The pinion gear 60 is in conjunction with the suction port cover 10 by a conjunction mechanism described later, and turns in a constant direction in conjunction with the open/close operation of the suction port cover 10. Thus, by fitting the pinion gear 60 and the rack gear 52*a* in the spiral pattern, the rotational motion of the pinion gear 60 is transformed into a linear motion along the rack gear 52*a* in the spiral pattern. The position of the pinion gear 60 itself is fixed in the inhaler 100, and although the pinion gear 60 turns in the constant direction with a rotation shaft as the center, the position of the rotation shaft does not change by the turning. On the other hand, in accordance with the turning of the fixed pinion gear 60, the position of the counter dial 50 varies along the rack gear 52*a*. The variation direction of the position of the counter dial 50 is preferably restricted by the slide lane 70.

The slide lane 70 is an element for restricting the movement direction of the counter dial 50 in the constant direction. In this embodiment, the slide lane 70 is disposed on the upper lid 31 of the casing 30. The slide lane 70 is disposed at a position abutting on the outer peripheral edge of the counter dial 50. In view of this, when the counter dial 50 starts moving in accordance with the turning of the pinion gear 60, the counter dial 50 gradually moves in the direction of extending the slide lane 70 while sliding along the slide lane 70. The extending direction of the slide lane 70 only needs to be appropriately designed considering a space before and after the movement of the counter dial 50.

As illustrated in FIG. 4(*a*), the position of the window portion 21*a* formed in the top cover 21 of the housing 20 is immovable. For example, as illustrated in FIG. 4, the window portion 21*a* is preferably disposed immediately above the pinion gear 60. However, as long as the window portion 21*a* is at the position overlapping with the counter dial 50 through before and after the movement of the counter dial 50 and at the position overlapping on the imaginary line in the spiral pattern connecting the numbers of remaining drugs 51*a* represented on the counter dial 50, the window portion 21*a* can be disposed not limited to be immediately above the pinion gear 60. Thus, since the position of the window portion 21*a* is immovable, when the counter dial 50 moves in the constant direction in accordance with the turning of the pinion gear 60, the number of remains 51*a* that can be visually perceived through the window portion 21*a* changes. Specifically, FIG. 4(*a*) and FIG. 4(*b*) schematically illustrate a state in which the relative positional relationship between the counter dial 50, the pinion gear 60, the slide lane 70, and the window portion 21*a* varies in accordance with the movement of the counter dial 50. From these drawings, a state in which the counter dial 50 moves in the constant direction while rotating along the slide lane 70 to count down the number of remaining drugs 51*a* by one visually perceived through the window portion 21*a* can be seen.

Subsequently, with reference to FIG. 3, the conjunction mechanism that causes the suction port cover 10 and the above-described counter mechanism to coordinate will be described in detail. Note that the conjunction mechanism illustrated in FIG. 3 also plays a role in causing the peeling mechanism of the two blister strips and the suction port cover 10 to coordinate at the same time. The conjunction mechanism is configured by including a hub gear 81, a ratchet gear 82, two index wheels 83*a*, 83*b*, two base spools 84*a*, 84*b*, four idler gears 85*a* to 85*d*, and a relay gear 86.

First, as illustrated in FIG. 3(*b*), when the suction port cover 10 is caused to transition from the closed state to the open state, the suction port cover 10 turns in the direction indicated by the arrow with a turning fulcrum as the center. The turning fulcrum of the suction port cover 10 is joined to the hub gear 81 disposed in the proximity of the center on the bottom lid 32 side of the casing 30. When the suction port cover 10 is turned at a constant angle, the hub gear 81 also turns at the same angle in the same direction as those of the suction port cover 10. The hub gear 81 is joined to the ratchet gear 82, and the ratchet gear 82 is fitted to the two idler gears (the first idler gear 85*a* and the third idler gear 85*c*). The ratchet gear 82 is configured so as to transmit the rotational motion in the constant direction of the hub gear 81 to the first and third idler gears 85*a*, 85*c*, but to idle to the two idler gears 85*a*, 85*c* and not to transmit the motion in the rotational motion in the opposite direction. Specifically, to cause the suction port cover 10 to transition from the closed state to the open state, the rotational motion of the hub gear 81 is transmitted to the first and third idler gears 85*a*, 85*c* via the ratchet gear 82. To cause the suction port cover 10 to transition from the open state to the closed state, the rotational motion of the hub gear 81 is not transmitted to the two idler gears 85*a*, 85*c*.

The ratchet gear 82 joined to the hub gear 81 is first coupled to the first index wheel 83*a* via the first idler gear 85*a*. That is, the rotational motion is transmitted in the order of the ratchet gear 82, the first idler gear 85*a*, and the first index wheel 83*a*. In view of this, while the first idler gear 85*a* turns in the opposite direction to the hub gear 81, the first index wheel 83*a* turns in the same direction as the hub gear 81. Additionally, the first idler gear 85*a* is coupled to the second index wheel 83*b* via the second idler gear 85*b*. That is, the rotational motion is transmitted in the order of the ratchet gear 82, the first idler gear 85*a*, the second idler gear 85*b*, and the second index wheel 83*b*. In view of this, while the second idler gear 85*b* turns in the same direction as the hub gear 81, the first idler gear 85*a* and the second index wheel 83*b* turn in the opposite direction to the hub gear 81. Thus, in conjunction with the operation of opening the suction port cover 10, the two index wheels 83*a*, 83*b* turn in the directions opposite to one another.

The index wheels 83*a*, 83*b* play a role in tearing off the backing sheet 220 from the blister strip 200. The rotation shafts of the respective index wheels 83*a*, 83*b* are engaged with the proximity of the starting end portion of the backing sheet 220 (or the base portion sheet 210) of the blister strips 200 in the casing 30. Turning the index wheels 83*a*, 83*b* provides tensile force for separating the backing sheet 220 from the base portion sheet 210 to the blister strip 200. The peeling mechanism is configured such that, by tearing off the backing sheet 220 from the two blister strips 200 approximately simultaneously by the two index wheels 83*a*, 83*b*, the drugs taken out from the blister strips 200 are mixed in the manifold 42.

On the other hand, the ratchet gear 82 joined to the hub gear 81 is also coupled to the first base spool 84*a* via the third idler gear 85*c*. That is, the rotational motion is transmitted in the order from the ratchet gear 82, the third idler gear 85*c*, and the first base spool 84*a*. In view of this, while the third idler gear 85*c* turns in the opposite direction to the hub gear 81, the first base spool 84*a* turns in the same direction as the hub gear 81. The third idler gear 85*c* is coupled to the second base spool 84*b* via the fourth idler gear 85*d*. That is, the rotational motion is transmitted in the order from the ratchet gear 82, the third idler gear 85*c*, the fourth idler gear 85*d*, and the second base spool 84*b*. In view of this, while the fourth idler gear 85*d* turns in the same direction as the hub gear 81, the third idler gear 85*c* and the second base spool 84*b* turn in the opposite direction to the hub gear 81. Thus, in conjunction with the operation of opening the suction port cover 10, the two base spools 84*a*, 84*b* turn in the directions opposite to one another.

The base spools 84*a*, 84*b* play a role in letting out the blister strip 200 toward the index wheels 83*a*, 83*b* side described above. The rotation shafts of the respective base spools 84*a*, 84*b* are engaged with the proximity of the terminating end portion of the blister strip 200 in the casing 30. Additionally, in the state before start of use, the long blister strip 200 is wound around the rotation shafts of the respective base spools 84*a*, 84*b*. Then, turning the base spools 84*a*, 84*b* in conjunction with the operation of opening the suction port cover 10 sends out the blister strip 200 to the index wheels 83*a*, 83*b* side. In the peeling mechanism, the proximity of the starting end portion of the backing sheet 220 of the blister strip 200 is mounted on the rotation shafts of the index wheels 83*a*, 83*b*, and the proximity of the terminating end portion of the blister strip 200 is mounted on the rotation shafts of the base spools 84*a*, 84*b* such that looseness does not occur by providing constant tensile force from the starting end portion to the terminating end portion.

Additionally, as illustrated in FIG. 3, in this embodiment, the rotation shaft of the second base spool 84*b* extends from the bottom lid 32 to the upper lid 31 of the casing 30 so as to penetrate in the thickness direction. Additionally, the rotation shaft of the second base spool 84*b* is joined to the center of the relay gear 86 disposed on the upper lid 31 side of the casing 30 to also function as the rotation shaft of the relay gear 86. Then, the relay gear 86 is fitted to the pinion gear 60 constituting the above-described counter mechanism. In view of this, when the second base spool 84*b* turns in accordance with the operation of opening the suction port cover 10, in conjunction with this, the turning motion is transmitted in the order of the relay gear 86, the pinion gear 60, and the counter dial 50. Note that in the illustrated embodiment, the second base spool 84*b* and the relay gear 86 are connected, but the first base spool 84*a* and the relay gear 86 can be connected. Thus, in the inhaler 100 according to this embodiment, the suction port cover 10 coordinates with the counter mechanism and the peeling mechanism via the conjunction mechanism. Note that in this embodiment, it is adjusted that the operation of opening the suction port cover 10 once counts down (or counts up) the representation of the number of remains of the counter dial 50 that can be visually perceived through the window portion 21a by one. This is easily achievable by appropriately adjusting the size of the gear and the interval of the number of remains represented on the counter dial 50.

Note that in the above-described embodiments, an example in which the suction port cover 10 is in conjunction with the peeling mechanism and this configures the blister opening means has been described, but the blister opening means of the present invention is not limited to this. For example, separately from the suction port cover 10, a lever that can be manually raised or lowered is disposed, and the peeling mechanism can be caused to coordinate with the lever. In this case, the suction port cover 10 need not to be coordinated with the peeling mechanism. For how to use, after the lever is lowered to drive the peeling mechanism, the suction port cover 10 may be opened to ensure inhaling the drug, or after the suction port cover 10 is opened, the lever may be lowered to drive the peeling mechanism to ensure inhaling the drug. Besides, the one coordinated with the peeling mechanism is not limited to the suction port cover 10 or the lever. In addition to them, a button type and a grip type can be employed.

In Description of this application, the embodiments of the present invention have been described by referring to the drawings to express the contents of the present invention. However, the present invention is not limited to the embodiments described above, but includes changed configurations and improved configurations obvious to those skilled in the art based on the matters described in Description of this application.

INDUSTRIAL APPLICABILITY

The present invention relates to an inhaler of powdered drug or a counter mechanism thereof. Accordingly, the present invention can be, for example, used in the pharmaceutical industry.

DESCRIPTION OF REFERENCE SIGNS

| | | | |
|---|---|---|---|
| 10 | suction port cover | 20 | housing |
| 21 | top cover | 21a | window portion |
| 22 | bottom cover | 30 | casing |
| 31 | upper lid | 32 | bottom lid |

-continued

| | | | |
|---|---|---|---|
| 40 | mouthpiece | 41 | suction port |
| 42 | manifold | 50 | counter dial |
| 51 | front surface | 51a | the number of remains |
| 52 | back surface | 52a | rack gear |
| 60 | pinion gear | 70 | slide lane |
| 81 | hub gear | 82 | ratchet gear |
| 83a, 83b | index wheel | 84a, 84b | base spool |
| 85a to 85d | idler gear | 86 | relay gear |
| 100 | inhaler | 200 | blister strip |
| 210 | base portion sheet | 211 | blister |
| 220 | backing sheet | | |

The invention claimed is:

1. An inhaler for gradually tearing off a backing sheet from one or a plurality of blister strips by blister opening means and sequentially supplying powdered drug by one dose amount to a space configured to inhale through a suction port, the inhaler comprising:

a counter mechanism for presenting a number of remaining drugs individually packed by the blister strip in conjunction with an operation of the blister opening means, wherein the counter mechanism includes:

a counter dial having a back surface side on which a rack gear in a spiral pattern is formed and a front surface side on which information displaying the number of remaining drugs is aligned in a spiral pattern and represented along the rack gear; and a pinion gear fitted to the rack gear and turning in a constant direction in conjunction with the operation of the blister opening means.

2. The inhaler according to claim 1, wherein a housing of the inhaler includes a window portion for visually perceiving one piece of the information displaying the number of remaining drugs represented on the counter dial from outside the housing.

3. The inhaler according to claim 1, wherein the counter mechanism further includes a slide lane that restricts a movement direction of the counter dial to a constant direction when the pinion gear turns.

4. A counter mechanism comprising:

a counter dial having a back surface side on which a rack gear in a spiral pattern is formed and a front surface side on which information displaying a number of usages is aligned in a spiral pattern and represented along the rack gear; and a pinion gear fitted to the rack gear and turning in a constant direction in conjunction with a use operation.

\* \* \* \* \*